United States Patent [19]

Kollenbrandt et al.

[11] Patent Number: 5,316,350
[45] Date of Patent: May 31, 1994

[54] COUPLING DEVICE FOR A TUBE SYSTEM

[75] Inventors: Norbert Kollenbrandt, Berkenthin; Heiko Schwenke, Lübeck; Elmar Wimmers, Hemmelsdorf, all of Fed. Rep. of Germany

[73] Assignee: Dragerwerk Aktiengesellschaft, Lubeck, Fed. Rep. of Germany

[21] Appl. No.: 868,479

[22] Filed: Apr. 14, 1992

[30] Foreign Application Priority Data

Apr. 26, 1991 [DE] Fed. Rep. of Germany ....... 4113707

[51] Int. Cl.⁵ ............................................. F16L 35/00
[52] U.S. Cl. .................................. 285/242; 285/921; 285/255; 285/914
[58] Field of Search ............... 285/242, 255, 319, 914, 285/921

[56] References Cited

U.S. PATENT DOCUMENTS

| | | | |
|---|---|---|---|
| 2,386,562 | 10/1945 | Mahoney | 285/180 |
| 3,167,331 | 1/1965 | Marshall | 285/255 |
| 3,245,703 | 4/1966 | Manly | 285/921 |
| 3,860,268 | 1/1975 | Zeman | 285/255 |
| 4,583,769 | 4/1986 | Bortolin | 285/921 |
| 4,708,375 | 11/1987 | Saur | 285/921 |
| 4,730,856 | 3/1988 | Washizu | 285/921 |
| 4,790,567 | 12/1988 | Kawano et al. | 285/921 |
| 4,844,512 | 7/1989 | Gahwiler | 285/921 |
| 4,903,995 | 2/1990 | Blenkush et al. | 285/255 |
| 4,969,667 | 11/1990 | Sauer | 285/921 |
| 4,969,669 | 11/1990 | Sauer | 285/921 |

FOREIGN PATENT DOCUMENTS

| | | | |
|---|---|---|---|
| 2657215C3 | 7/1979 | Fed. Rep. of Germany | F16L 37/12 |
| 3623367C2 | 7/1989 | Fed. Rep. of Germany | A61M 16/08 |
| 255789 | 10/1989 | Japan | 285/255 |

Primary Examiner—Eric K. Nicholson
Attorney, Agent, or Firm—McGlew and Tuttle

[57] ABSTRACT

A coupling device for establishing a detachable connection for a tube system is to be improved so that while simple detachability of the pipe socket and tube is guaranteed, the pulling-off force is equivalent to firm clamping. To accomplish the task, a sleeve-like coupling box 7 is provided, which surrounds the tube 5 in a clamp-like manner and, for fixation on the pipe socket 2, it has, on the inside, a circumferential notch 8, into which two oppositely arranged projecting parts 4 of the pipe socket 2 snap. The coupling box 7 expands under the effect of a force acting laterally, so that the projecting parts 4 will disengage from the notch 8.

7 Claims, 3 Drawing Sheets

1

COUPLING DEVICE FOR A TUBE SYSTEM

FIELD OF THE INVENTION

The present invention pertains to a coupling device for establishing a detachable connection between two parts of a tube system, particularly a respiration system, the first part of which is a pipe socket with an undercut, and the second part of which is a tube with a locking member engaging in the undercut.

BACKGROUND OF THE INVENTION

A coupling device of this type has become known from DE-C2-36,23,367. The prior-art coupling device is used to connect a tube to the pipe socket of an anesthesia device or respirator. On its inside, the tube has a locking member which is designed as an elastic lip and snaps into an undercut when pushed over the pipe socket. The coupling device is designed such that even though the tube is in firm contact with the pipe socket during respiration, it is possible to rapidly remove the tubes from the pipe socket in the case of an emergency. The locking member is expanded radially by the axial pulling force acting on the tube to the extent that it will slide out of the undercut and the coupling device will thus be detached.

Coupling devices have also been known from the connection of respiration tubes in gas masks and breathing apparatus. It is required here for the respiration tubes to be firmly connected to the corresponding pipe socket during operation, but rapid separation is desirable during the preparation of the apparatus for use. To achieve this, the tube is firmly clamped onto the corresponding pipe socket, which means a large amount of mounting work. However, the tube may be damaged by tightening the clamps too tightly, and it is often difficult to work with a tool in breathing apparatus of compact design.

A quickly detachable coupling described in DE-C3,26,57,215 consists of a pipe socket that is provided with a circumferential notch and a tube with a coupling box, at the end of which opposite projecting parts, which snap into the notch of the pipe socket in the assembled state, are provided. The coupling box is made of elastic material in the area of the projecting parts and is provided with pressure-absorbing areas which are arranged offset by 90° in relation to the projecting parts. On compression of the pressure-absorbing areas, the coupling box is expanded to the extent that the projecting parts will slide out of the notch.

Even though the prior-art coupling permits the tube and pipe socket to be joined rapidly, the connection is able to absorb only limited pulling-off forces. The outer, flexible part of the coupling box expands radially and the projecting parts slide out of the notch in the case of stronger pulling-off forces. In addition, such a coupling is expensive to manufacture, because complicated plastic parts, which are shaped correspondingly to fit one another and must be manufactured with close tolerances, are needed.

SUMMARY AND OBJECT OF THE INVENTION

The basic task of the present invention is to improve a coupling device so that while simple detachability of the pipe socket and tube is guaranteed, the pulling-off force is equivalent to firm clamping of the tube on the pipe socket.

The task is accomplished by providing a sleeve-like coupling box which surrounds the tube in a clamp-like manner as a retaining ring in the area of the locking member, and for fixation on the pipe socket, it has, on the inside, a circumferential notch, into which two oppositely arranged projecting parts of the pipe socket snap in, and at least in the area of the notch, the coupling box is so flexible that under the effect of pressure in the transverse direction, it will expand at right angles to the projecting parts to the extent that the projecting parts will disengage from the notch and release the coupling box.

The advantage of the present invention is essentially the fact that due to the coupling box being pushed over the locking member, the tube is prevented from radially expanding in this area, such that the locking member will remain in the undercut. For the locking member, the coupling box has the function of a fixed clamping. The coupling box is fixed on the tube so that the projecting parts of the pipe socket will snap into the opposite notch of the coupling box. To rapidly separate the tube connection, the coupling box is widened elliptically by exerting a lateral pressure until the projecting parts exit the notch, and the coupling box can be pushed away from the pipe socket over the tube. The projecting parts on the pipe socket are arranged opposite each other, offset by 180°, and the direction of application of the force is perpendicular to the projecting parts. The locking member on the inside of the tube may be designed as a circumferential bead or in the form of individual, bead-like sections. To code the coupling device, it is advantageous to provide pipe sockets with connection pieces of lengths L1 and L2, and to design the tubes at the tube ends with corresponding tube connections of lengths L1 and L2. Coding of the coupling device may be necessary to prevent tubes, e.g., the inspiration tube and the expiration tube in a breathing apparatus, from being erroneously interchanged.

As a mounting aid for pushing the tubes over the pipe sockets, it is useful to design the connection pieces and the tube connections as conical connections. When pushing over the tube, the locking member is gradually expanded due to the conicity of the socket connection, and will snap into the undercut of the pipe socket.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
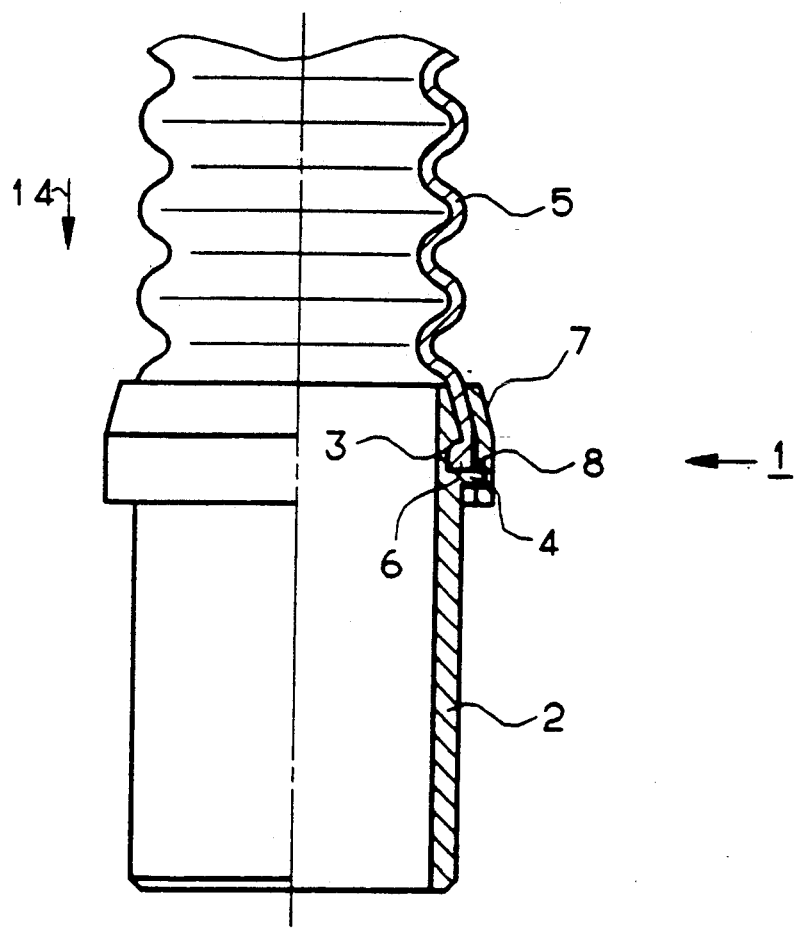
FIG. 1 is a partially cutaway side view of a coupling device according to the invention.

The coupling device 1 shown in FIG. 1 consists of pipe socket 2 with two projecting parts 4, one of which is shown in FIG. 1, and of a tube 5 with a locking member 6, which is received by an undercut 3 of the pipe socket 2. In the area of the locking member 6, the tube 5 is secured in a clamp-like manner by a coupling box 7, which is in contact with the tube 5. The coupling box 7 is provided on the inside with a circumferential notch 8, into which the projecting parts 4 snap, as a result of which the location of the coupling box 7 on the tube 5 is fixed.

Figure 2:
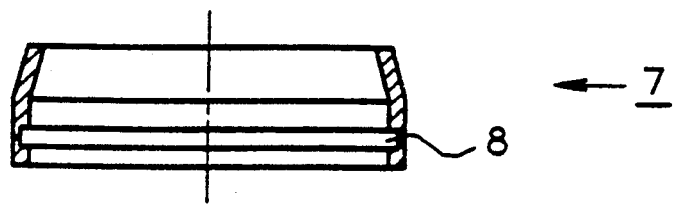
FIG. 2 is a sectional side view of a coupling box according to the invention.

FIG. 2 shows a sectional side view of the coupling box 7. The circumferential notch 8 from FIG. 1 is recognizable on the inside.

Figure 3:
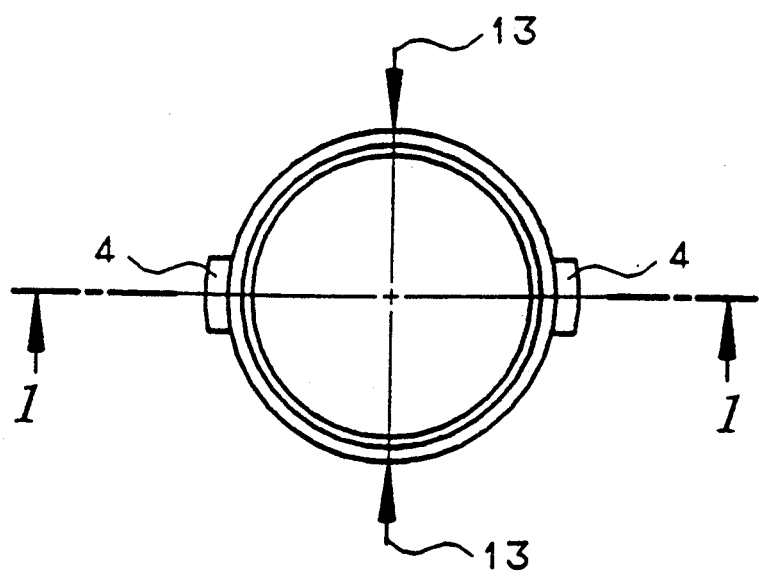
FIG. 3 is a top view of a pipe socket according to the invention.

FIG. 3 shows the top view of the pipe socket 2 from FIG. 1 with the two opposite projecting parts 4. The right-hand part of the sectional representation 1—1 in FIG. 3 corresponds to the right-hand, cutaway part in FIG. 1.

The coupling device 1 according to FIG. 1 is assembled as will be described below.

The tube 5 is first pushed over the front part of the pipe socket 2 until the locking member 6 snaps into the undercut 3 (FIG. 1). The coupling box 7 is then pushed over the tube 5 along the arrow 14 indicating the direction of pushing, until the projecting parts 4 snap into the notch 8.

To separate the coupling device 1, the coupling box 7 is compressed in the direction of arrow 13 (see FIG. 3), as a result of which its cross section will be elliptically deformed, and the two projecting parts 4 will spring out of the notch 8. The coupling box 7 can now be pushed off the tube 5 in the direction of the arrow 14 (see FIG. 1) indicating the direction of pushing. The tube 5 is subsequently pulled from the pipe socket 2, and the locking member 6 will spring out of the undercut 3.

Figure 4:
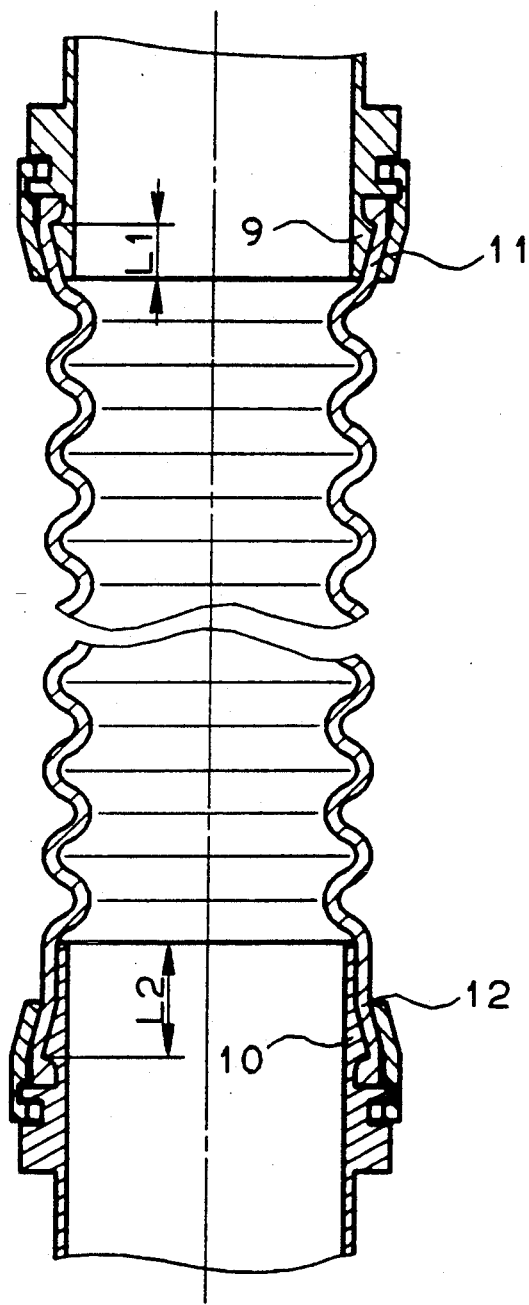
FIG. 4 is a sectional side view of a coded coupling device.

FIG. 4 shows the sectional side view of a coded coupling device. The difference from the coupling device 1 shown in FIG. 1 is the fact that the pipe sockets 2 are provided with a first connection piece 9 of length L1 and a second connection piece 10 of length L2, over which a first tube connection 11 of length L1 and a second tube connection 12 of length L2, respectively, are pushed. Coding is achieved in this case such that, even though the second tube connection 12 can be pushed over the first connection piece 9, the first tube connection 11 does not, conversely, fit the second connection piece 10. The connection pieces 9, 10 and the tube connections 11, 12 have corresponding conical designs in the overlapping zone in order to simplify mounting of the tube 5. When pushing the tube connections 11, 12 over the corresponding connection pieces 9, 10, the locking member 6 (FIG. 1) is gradually expanded due to the conicity of the connection pieces 9, 10, until it snaps into the undercut 3 (FIG. 1).

What is claimed is:

1. A coupling device for producing a detachable connection between two parts of a tube system, comprising: a pipe socket including an undercut and two substantially oppositely arranged projecting parts; a tube including a locking member engaging said undercut of said pipe socket; a sleeve-shaped coupling box encompassing said tube in a clamping manner, adjacent said locking member, said coupling box forming a retaining ring including a circumferential notch on an interior side, wherein said two oppositely arranged projecting parts of said pipe socket engage said circumferential notch flexing engagement and disengagement means including a flexible region of said coupling box at least in an area of said circumferential notch, allowing said coupling box to be expanded upon exerting pressure in a transverse direction, perpendicular to said projecting parts, thereby allowing disengagement of said projecting parts from said circumferential notch to release said coupling box.

2. A coupling box according to claim 1, further comprising: coding means including a connection piece on said pipe socket having a defined length from a front end of said pipe socket to said undercut, said tube having a tube connection of a defined length wherein coupling of said pipe to said tube requires said tube connection defined length to be substantially equal to said pipe socket connection piece defined length.

3. A coupling box according to claim 1, wherein: said tube includes a first end with a first tube connection and a second end with a second tube connection, said first tube connection including said locking member and said coupling box, said second tube connection including a second tube connection locking member and a second tube connection coupling box wherein said second tube connection coupling box includes a second tube connection circumferential notch on an inner side of said second tube connection coupling box and further comprising a second pipe socket and connection means including a first connection piece of a defined length on said pipe socket and a second connection piece of a second defined length provided with said second pipe socket, said first tube connection being of said first defined length and said second tube connection being of said second defined length for allowing connection of said first tube connection only to said first connection piece and said second tube connection only to said second connection piece.

4. A coupling device according to claim 3, wherein said first connection piece and said second connection piece and said coupling box and said second coupling box are designed corresponding conically in an overlapped area.

5. A coupling device for producing a detachable connection between two parts of a tube system, comprising: a pipe socket including an undercut and two substantially oppositely arranged projecting parts; a tube including a locking member engaging said undercut of said pipe socket; a sleeve-shaped coupling box encompassing said tube in a clamping manner, adjacent said locking member, said coupling box forming a retaining ring including a circumferential notch on an interior side, wherein said two oppositely arranged projecting parts of said pipe socket engage said circumferential notch, said coupling box being formed to include a flexible region at least in an area of said circumferential notch, allowing said coupling box to be expanded upon exerting pressure in a transverse direction, perpendicular to said projecting parts, thereby allowing disengagement of said projecting parts from said circumferential notch to release said coupling box, said tube includes a first end with a first tube connection and a second end with a second tube connection, said first tube connection including said locking member and said coupling box, said second tube connection including a second tube connection locking member and a second tube connection coupling box wherein said second tube connection coupling box includes a second tube connection circumferential notch on an inner side of said second tube connection coupling box and further comprising a second pipe socket and connection means including a first connection piece of a defined length on said pipe socket and a second connection piece of a second defined length provided with said second pipe socket, said first tube connection being of said first defined length and said second tube connection being of said second defined length for allowing connection of said first tube connection only to said first connection piece and said second tube connection only to said second connection piece.

6. A coupling device for producing a detachable connection between two parts of a tube system, comprising: a pipe socket including an annular undercut and two substantially oppositely arranged projecting parts; a tube including a locking member engaging said undercut of said pipe socket; a sleeve-shaped coupling box encompassing said tube in a comprising manner, adjacent said locking member, said coupling box forming a retaining ring including a circumferential notch on an interior side, wherein said two oppositely arranged projecting parts of said pipe socket engage said circumferential notch, said coupling box being formed to include flexing engagement and disengagement means include a flexible region of said coupling box at least in an area of said circumferential notch, allowing said coupling box to be expanded upon exerting pressure in a transverse direction, perpendicular to said projecting parts, thereby allowing disengagement of said projecting parts from said circumferential notch to release said coupling box, coding means including a connection piece on said pipe socket having a defined length from a front end of said pipe socket to said undercut, said tube having a tube connection of a defined length wherein coupling of said pipe to said tube requires said tube connection defined length to be substantially equal to said pipe socket connection piece defined length.

7. A coupling box according to claim 1, wherein said undercut is annular.

* * * * *